(12) United States Patent
Schmidt et al.

(10) Patent No.: US 8,777,134 B2
(45) Date of Patent: Jul. 15, 2014

(54) SUSPENSION COMPRISING BENZIMIDAZOLE CARBAMATE AND A POLYSORBATE

(75) Inventors: Carsten Schmidt, Schwabenheim (DE); Mark Allan, Schwabenheim (DE); Elizabeth Benedicte Daniele Deschamps, Schwabenheim (DE)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 13/424,257

(22) Filed: Mar. 19, 2012

(65) Prior Publication Data

US 2012/0213830 A1    Aug. 23, 2012

Related U.S. Application Data

(63) Continuation of application No. 12/304,486, filed as application No. PCT/EP2007/055794 on Jun. 13, 2007, now abandoned.

(60) Provisional application No. 60/813,928, filed on Jun. 14, 2006.

(30) Foreign Application Priority Data

Jun. 14, 2006   (EP) .................................... 06115495

(51) Int. Cl.
| | | |
|---|---|---|
| *A61K 31/4184* | (2006.01) | |
| *A61K 9/14* | (2006.01) | |
| *A61P 33/00* | (2006.01) | |
| *B82B 1/00* | (2006.01) | |
| *A61K 9/00* | (2006.01) | |
| *A61K 9/10* | (2006.01) | |

(52) U.S. Cl.
CPC ............... *A61K 9/0095* (2013.01); *A61K 9/10* (2013.01); *Y10S 977/788* (2013.01); *Y10S 977/915* (2013.01)
USPC ............. 241/21; 514/395; 977/788; 977/915; 424/489

(58) Field of Classification Search
CPC ............................. A61K 9/0095; A61K 9/10
USPC ..................... 241/21; 514/395; 977/788, 915; 424/489
See application file for complete search history.

(56) References Cited

U.S. PATENT DOCUMENTS

| | | | |
|---|---|---|---|
| 3,480,642 A | 11/1969 | Stedman | |
| 3,574,845 A | 4/1971 | Actor et al. | |
| 3,657,267 A | 4/1972 | Van Gelder et al. | |
| 3,891,758 A | 6/1975 | Hannah | |
| 3,915,986 A | 10/1975 | Gyurik et al. | |
| 3,929,821 A | 12/1975 | Beard et al. | |
| 3,954,791 A | 5/1976 | Loewe et al. | |
| 3,993,682 A | 11/1976 | Kolling et al. | |
| 4,406,893 A | 9/1983 | Nafissi-Varchei | |
| 4,639,463 A | 1/1987 | Rosner et al. | |
| 5,145,684 A | 9/1992 | Liversidge et al. | |
| 5,459,155 A | 10/1995 | Banks | |
| 6,093,734 A | 7/2000 | Garst et al. | |
| 7,893,271 B2 | 2/2011 | Chassaing | |
| 2005/0118271 A1 | 6/2005 | Schliecker et al. | |
| 2009/0131369 A1 | 5/2009 | Chassaing | |

FOREIGN PATENT DOCUMENTS

| | | |
|---|---|---|
| EP | 0 093 497 | 11/1983 |
| EP | 1214052 B1 | 8/2004 |
| EP | 1 913 009 B1 | 5/2010 |
| FR | 2 336 931 | 12/1975 |
| GB | 2 307 871 | 6/1997 |
| WO | WO 93/12124 | 6/1993 |
| WO | WO 95/13065 | 5/1995 |
| WO | WO 95/16447 | 6/1995 |
| WO | WO 00/50009 | 8/2000 |
| WO | WO 01/17504 | 3/2001 |
| WO | WO 02/080678 A1 | 10/2002 |
| WO | WO 2007/014846 | 2/2007 |
| WO | WO 2007/067470 A2 | 6/2007 |
| WO | WO 2007/144362 | 12/2007 |
| WO | WO 2010/045700 | 4/2010 |

OTHER PUBLICATIONS

Dhaneshwar et al., Synthesis and anthelmintic activity of some mannich bases of fenbendazole and albendazole, Indian Drugs, 1990, pp. 24-26, vol. 28, No. 1.
Hernandez-Luis et al., Synthesis and hydrolytic stability studies of albendazole carrier prodrugs,Bioorganic & Medicinal Chemistry Letters, 2001, pp. 1359-1362, vol. 11.
International Search Report PCT/EP2007/055794 dated Sep. 5, 2007.
Klocking et al., Uber die pharmakolgie des antifibrinolytikums paminomethylbenzoesaure, Haematologia, 1970, pp. 175-179, Suppl. 1.
McKellar et al., The benzimidazole anthelmintic agents—a review, J. Vet. Pharmacol. Therapy., 1990, pp. 223-245, vol. 13.
Nielsen, L.S., Improved peroral bioavailability of mebendazole in rabbits by administration of various Nalkoxycarbonyl derivatives of mebendazole, Int'l Journal of Pharamceutics, 1994, pp. 175-179, vol. 104.
PCT International Search Report for International Application No. PCT/EP2007/055794, mailed Sep. 5, 2007, 3 pages.
PCT Written Opinion for International Application No. PCT/EP2007/055794, mailed Sep. 5, 2007, 7 pages.

*Primary Examiner* — Mina Haghighatian

(57) ABSTRACT

This invention is directed to a pharmaceutical composition for drinking water administration comprising benzimidazole carbamate particles having an effective average particle size of less than 450 mm and a Tween-type surfactant; a method for making the composition; use of the composition to make a medicament for controlling parasites; and use of said composition for the manufacture of a medicament or protecting animal from parasitic infection.

18 Claims, 6 Drawing Sheets

SUSPENSION COMPRISING BENZIMIDAZOLE CARBAMATE AND A POLYSORBATE

CROSS-REFERENCE TO RELATED APPLICATIONS

This is a continuation of U.S. patent application Ser. No. 12/304,486 filed on Mar. 31, 2009, now abandoned titled A SUSPENSION COMPRISING BENZIMIDAZOLE CARBAMATE AND POLYSORBATE, which is a nation phase entry under 35 U.S.C. §371 of international Patent Application No. PCT/EP2007/055794, filed Jun. 13, 2007, published in English as International Publication No. WO2007/0144362, which claims the benefit under Article 8 of the Patent Cooperation Treaty to European Patent Application No. 06115495.1, filed Jun. 14, 2006 and U.S. Patent Application No. 60/813,928, filed Jun. 14, 2006. The entire contents of each of the above-referenced patent applications are hereby incorporated by reference into this patent.

FIELD OF THE INVENTION

This invention is generally related to a pharmaceutical composition for drinking water administration comprising a benzimidazole carbamate, a method for making the composition, use of the composition to make a medicament for controlling a parasite in an animal, and a method of using the composition to protect an animal from a parasitic infection.

BACKGROUND OF THE INVENTION

Benzimidazoles were originally developed as plant fungicides and later as veterinary and human anthelmintics (e.g., dewormers). The family of benzimidazoles with anthelmintic activity includes thiazolyl benzimidazoles and benzimidazole carbamates. The benzimidazoles show a broad spectrum of activity especially against helminth parasites (e.g., roundworms or tapeworms).

Well known benzimidazoles with activity against helminths are for example thiabendazole; cambendazole; and benzimidazole carbamates, such as parbendazole, mebendazole, flubendazole, fenbendazole, oxfendazole, oxibendazole, albendazole, ricobendazole and luxabendazole, all of which differ in the substituents on the parent benzimidazole nucleus.

Phenylguanidine prodrugs that are metabolically transformed into anthelmintic benzimidazoles have also been developed. Febantel, for example, is a prodrug that is converted into fenbendazole, and netobimin yields albendazole.

Benzimidazole carbamates are generally poorly soluble in water. For some useful applications of the compounds the poor water solubility of the benzimidazoles is a major obstacle.

Fenbendazole (FBZ) is a benzimidazole carbamate used as veterinary anthelmintic in many species, including poultry, pigs and cattle. Fenbendazole is used to control nematodes such as *Ascaridia* sp., *Heterakis* sp. and *Capillaria* sp. in poultry and pigs.

The mass administration of poorly water soluble medicaments like benzimidazole carbamates to intensively reared pigs and poultry has so far been limited to oral administration as a top dressing on the feed or admixed into the feed. Such medicated feed, needs to be, however, separately prepared on the farm or in a feed mill and there is always the risk of cross contamination of non-medicated feed. The top-dressing, on the other hand, requires additional labour.

Therefore medication via drinking water systems is preferred to be routinely used for de-worming of intensively reared animals because of the easiness of administration to a number of animals at the same time.

Many pig and poultry farms are already equipped with the necessary devices to administer medication via drinking water systems. Such drinking water systems on farms are complex systems of tanks, pipes, coils, pen drinkers and nipples. An average stable may contain hundreds of meters of pipes with many coils and hundreds of individual cups and/or nipples. The water in the drinking water system in a pig or poultry house obeys the principles of laminar flow through the pipes and coils and is subjected to the so called "shearing "forces which will affect the rate of flow. In such complex piping system there are considerable risks for segregation or sedimentation of the medication, certainly when it concerns water insoluble compounds.

The effectiveness of medication via the drinking water system in general largely depends on the quality of the composition and the palatability of the medication. Such composition should provide maximum availability of the active ingredient, minimal segregation and sedimentation of the active compound in the drinking water system, medication pumps, nipples cups etc., a very precise dosing and homogeneous distribution of the active compound in the drinking water and a guaranteed stability of the active compound.

Up to present, no convenient solution has been available for this route of medication of farm animals for poorly water soluble veterinary drugs, like benzimidazole carbamates, that meets these requirements.

International Patent application WO 95/13065 discusses an aqueous fenbendazole suspension composition with a Tween-type surfactant and a preservative. In this aqueous suspension fenbendazole remains in suspension and no agglomeration or change in particle size occurs if it has been stored for a period of time. The particle size is in the order of about 1 micron. This aqueous suspension of fenbendazole is, however, not suitable for administration through a watering system as it is used in big pig or poultry houses as described above. It shows sedimentation after a certain period of time if it is diluted to a drinking water concentration of 60 ppm fenbendazole. These sediments do not allow a homogeneous distribution of the fenbendazole in the watering system and pose the risk of blocking of watering system equipment e.g. of drinking nipples.

International Patent application WO 01/17504 discusses a suspo-emulsion composition for drinking water administration. These compositions do however not fulfil the requirements for administration in drinking water systems concerning homogeneous distribution.

International Patent application WO 00/50009 discusses encapsulating water-labile or -insoluble compounds in liposomes for drinking water administration.

International Patent application WO 95/16447 discusses anthelmintic compositions comprising micronised particles of rafoxanide and fenbendazole with more than 98% of the particles having an average particle size of less than 20 micron for oral administration, but not in drinking water systems.

UK Patent application GB 2307871 discusses an industrial scale process for formulating aqueous oxfendazole suspensions without employing any particle size reduction techniques.

SUMMARY OF THE INVENTION

This invention generally relates to stable, efficacious, aqueous compositions of benzimidazole carbamates that can be conveniently administered via drinking water systems.

Thus, this invention provides, in part, a pharmaceutical composition for drinking water administration of benzimidazole carbamates. This composition is characterized in that it comprises an aqueous suspension comprising benzimidazole carbamate particles having an effective average particle size of less than about 450 nm, and a Tween-type surfactant.

This invention also provides, in part, a use of the above composition for making a medicament for controlling a parasite in an animal by administering the medicament via the animal's drinking water.

This invention also provides, in part, a method for preparing a pharmaceutical composition for drinking water administration. The method comprises:

i. dispersing benzimidazole carbamate particles in a pharmaceutically acceptable carrier comprising a Tween-type surfactant; and ii. mechanically reducing the particle size of the benzimidazole carbamate particles to an effective average particle size of less than about 450 nm.

This invention also provides, in part, a method for protecting an animal from a parasitic infection. This method comprises administering the above composition to the animal via the animal's drinking water. This protection includes preventing, reducing the risk of, delaying the onset of, reducing the spread of, ameliorating, suppressing, and/or eradicating the parasitic infection and/or one or more of its symptoms.

Further benefits of Applicants' invention will be apparent to one skilled in the art from reading this specification.

DETAILED DESCRIPTION OF PREFERRED EMBODIMENTS

Figure 1:
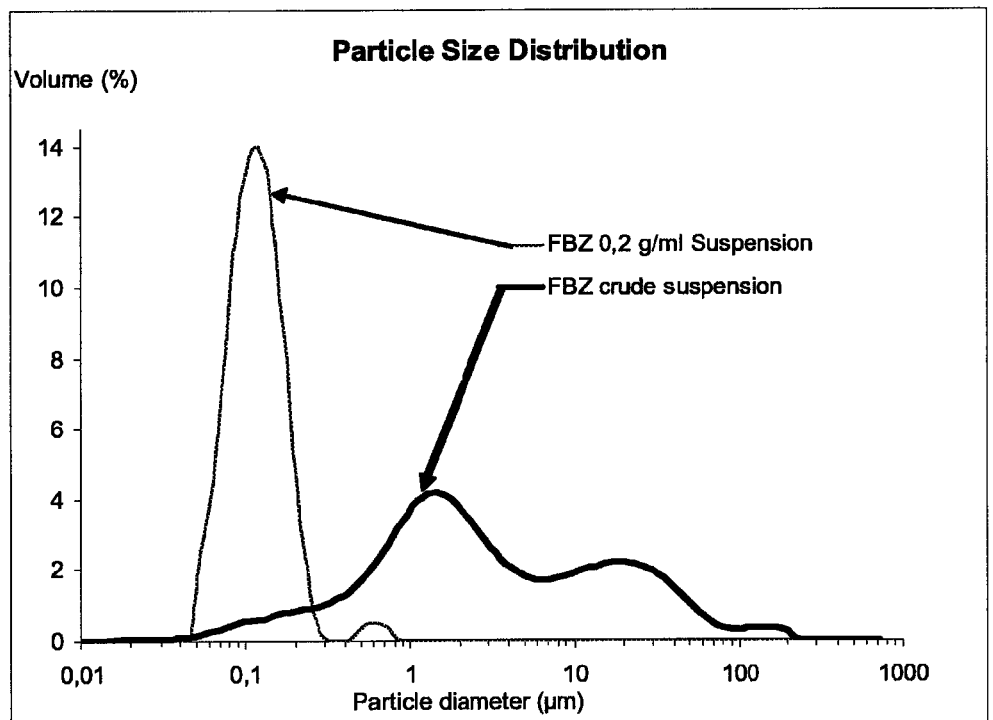
FIG. 1 represents the particle size distribution of Fenbendazole (FBZ) suspension without (crude) and after wet-milling

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

It has been shown by the current inventors that the composition according to the invention, that comprises an aqueous suspension comprising benzimidazole carbamate particles having an effective average particle size of less than about 450 nm, and a Tween-tupe surfactant is stable enough and can be distributed homogeneously in the system to allow the effective administration of benzimidazole carbamate compounds to animals through drinking water systems Through this new composition the benzimidazole carbamate can be delivered to the target animal through a drinking water system of choice by means of mixing and diluting the composition with water in the central water tank or separate storage tank.

Alternatively the composition is injected continuously into a high or low pressure ring system for drinking water distribution, using a dosage dispenser or dosing pump system or proportioner medication system.

Dosing pump systems rely on a pump that delivers measured amounts of a concentrate into the water pipes at a typical dilution of 1-5%. Within the dosing pump systems, electronic dosing pump systems such as KONTI-DOS from Buerkert or mechanical dosing pump such as DOSATRON® water powered dosing pump, DOSMATIC® water-driven, proportional medicators can be used. The variety of field installations also concerns the water supply systems themselves: dead end or closed loop systems in different lengths with different pipe materials (e.g. PVC, galvanized iron) and the drinkers which are adapted to the target animals such as bell drinkers, nipples.

In one embodiment the effective average particle size of the benzimidazole carbamate is less than about 450 nm or less than 400 nm, in another embodiment less than about 350 nm, or less than about 300 nm. In another embodiment the effective average particle size of the benzimidazole carbamate is less than about 250 nm, in another embodiment less than about 200 nm.

In one embodiment the effective average particle size of the benzimidazole carbamate is between about 50 nm and 450 nm, in another embodiment between about 100 nm and 400 nm, in another embodiment between about 150 and 350 nm, or between about 180 nm and 300 nm. In another embodiment the effective average particle size of the benzimidazole carbamate is between about 190 nm and 220 nm, in another embodiment about 200 nm.

Alternatively the benzimidazole carbamate can be formulated as an injectable product for parenteral administration to animals.

As used herein, particle size refers to a number average particle size as measured by conventional particle size measuring techniques well known to those skilled in the art, such as laser scattering, sedimentation field flow fractionation, photon correlation spectroscopy, or disk centrifugation.

The particle size measurement can be performed with a Malvern Mastersizer 2000 with the Hydro 2000G measuring cell, or with a Horiba LA-910 laser scattering particle size distribution analyzer.

By "an effective average particle size of less than about 450 nm" it is meant that at least 90% of the particles have a weight average particle size (D (0.90) of less than 450 nm when measured by the above-noted techniques.

Tween-type surfactants (Polysorbates, Sorbitan esters, poly(oxy-1,2 ethanediyl) derives, Tweens) are water soluble nonionic surface active agent comprised of complex esters and ester-ethers derived from hexahydric alcohols, alkylene oxides and fatty acids by adding polyoxyethylene chains to hydroxyl of sorbitol and hexitrol anhydrides (hexitans and hexides) derived from sorbitol and then partially esterifying with the common fatty acids such as lauric, palmitic, stearic and oleic acids.

In one embodiment the Tween-type surfactant is selected from one or more of Tween 20, Tween 40, Tween 60 or Tween 80, also known in the pharmaceutical industry as polysorbate 20, polysorbate 40, polysorbate 60 and polysorbate 80. Polysorbate 20 (Polyoxyethylated Sorbitan Monolaurate,) is a laurate ester, Polysorbate 60 (Polyoxyethylated Sorbitan Monostearate) is a mixture of stearate and palmitate esters; and Polysorbate 80 (Polyoxyethylated Sorbitan Monooleate) is an oleate ester.

Such Tween type surfactants are commercially available and/or can be prepared by techniques known in the art.

In one embodiment the Tween-type surfactant is polyoxyethylene sorbitan monoleate (polysorbate 80, Tween 80) having the chemical name polyoxyethylene (20) sorbitan monooleate, e.g. available from ICI Specialty Chemicals.

The Tween-type surfactant is present in the composition from about 0.1 to about 50% by weight. In some embodiments, the concentration of the Tween-type surfactant is from about 5% to about 20% by weight, from about 7.5% to about 15% by weight, or about 10%.

The composition according to the invention comprises one or more benzimidazole carbamates. Well known benzimidazole carbamates are e.g. parbendazole (see, e.g., U.S. Pat. No. 3,480,642), mebendazole (see, e.g., U.S. Pat. No. 3,657,267), flubendazole (see, e.g., U.S. Pat. No. 3,657,267), fenbendazole (see, e.g., U.S. Pat. No. 3,954,791), oxfendazole (see, e.g., U.S. Pat. No. 3,929,821), oxibendazole (see, e.g., U.S. Pat. No. 3,574,845), albendazole (see, e.g., U.S. Pat. No. 3,915,986), ricobendazole (albendazole sulfoxide) (see, e.g., U.S. Pat. No. 3,915,986) and luxabendazole (see, e.g., U.S. Pat. No. 4,639,463), all of which differ in the substituents on the parent benzimidazole nucleus or prodrugs like febantel and netobimin.

In one embodiment the benzimidazole carbamate is fenbendazole (see, e.g., U.S. Pat. No. 3,954,791). In another embodiment the benzimidazole carbamate is flubendazole (see, e.g., U.S. Pat. No. 3,657,267).

The benzimidazole carbamate is generally present in the composition in an amount of about 5 to about 50% by weight. In some embodiments, the benzimidazole carbamate is present at a concentration of from about 10% to about 40% by weight, from about 15% to about 30%, or from about 17.5% to about about 25% by weight or about 20%.

In some embodiments, the composition comprises a pharmaceutically acceptable carrier. The carrier may be, for example, an aqueous carrier, preferably (purified) water. However, the invention can be practiced with other liquid media in which the benzimidazole carbamate is poorly soluble and dispersible, e.g aqueous salt solutions.

Optionally, the composition may also contain an antifoaming agent, such as for example, simethicone emulsion 30% USP, sodium oleate, sodium caprylate or mixtures thereof. The antifoaming agent is present in sufficient concentration to prevent foam formation when the composition of the instant invention is diluted with water. In the instant invention the simethicone emulsion may be present at concentration of from about 0.2% by weight to about 1% by weight. In some embodiments, the simethicone emulsion is present at a concentration of about 0.5% by weight.

Optionally, the composition may also contain a preservative. The preservative is one known to those in the art, and can be e.g. benzyl alcohol, butylparaben sodium salt, methylparaben sodium salt, propylparaben sodium salt and mixtures thereof. It is generally present in an amount of from about 0.01% to about 3% by weight. In some embodiments, the benzyl alcohol is present at a concentration of from about 1.5% to about 2.5% by weight, or about 2% by weight.

One aspect of the current invention is the use of the composition according to the invention for the manufacture of a medicament for controlling a parasite in an animal by administering the medicament to the animal via the animal's drinking water.

The current invention provides a method for protecting an animal from a parasitic infection, wherein the method comprises administering the composition according to the invention to the animal via the animal's drinking water In one embodiment this composition can be used to treat animals, especially livestock animals (e.g., cattle, poultry and pigs) with benzimidazole carbamate compounds e.g. fenbendazole via drinking water systems. The composition (finished product) can be used in a proportioner or medicator to prepare medicated drinking water as it is known in the art.

The medicator uses for example 1 oz of the finished product and further dilutes with water generally in about a 1:128 ratio to obtain medicated drinking water having a benzimidazole carbamate e.g. fenbendazole concentration of from about 10 to about 150 ppm.

In some embodiments, the benzimidazole carbamate, e.g. fenbendazole concentration in the medicated drinking water is from about 40 to about 120 ppm, depending on the effective dose, the animal body weight, the animal water consumption and the treatment period.

In one embodiment, the concentrated premix composition is diluted directly to a concentration of from about 10 ppm to about 150 ppm. In some embodiments the concentrated premix composition is diluted directly to a concentration of from about 40 to about 120 ppm of the benzimidazole carbamate e.g. fenbendazole, and used for drinking water administration (e.g., for poultry) directly.

In one specific embodiment for the specific benzimidazole carbamate fenbendazole, the concentration is calculated to provide the targeted amount of fenbendazole per body weight (BW) of the poultry being treated in the range of from about 1 mg to about 5 mg of fenbendazole per kilogram of body weight per day in the volume of drinking water normally consumed by the poultry being treated in a 2 to 24 hour treatment period. The targeted dosage is dictated by the parasitic species infection being treated and is known in the art. For the administration to other species the concentration is calculated respectively.

The medicated drinking water is used to treat the poultry for from about 2 to about 24 hour treatment periods, often preferably about 8 hour treatment periods on one to six consecutive days. For the administration to other species the treatment period is calculated respectively.

To treat pigs the finished product is diluted to achieve the desired concentration so as to obtain drinking water containing an efficacious amount of benzimidazole carbamates, such as e.g. fenbendazole to control helminths in pigs. The efficacious amount is dependent on the parasites species infestation being treated and is known in the art.

Alternatively the composition according to the current invention can be administered parenterally to animals, e.g. by intraveneous, intramuscular or subcutaneous injection.

In another aspect the current invention provides a method for protecting an animal from a parasitic infection, wherein the method comprises administering the composition according to the invention to the animal via parenteral route Parenteral treatment via alternative routes is also possible. The parenteral administration route is especially useful in case plasma and tissue levels of the benzimidazole carbamate are important since, in order to act systemically, the benzimidazoles have to be taken up into the bloodstream. One such example is the use of the benzimidazoles in combatting systemic parasitic infections, for example with the larval stage of certain cestodes, e.g. *Echinococcus mullicularis* and *E. granulosis*.

In general the composition according to the current invention can be administered to all species of animals that need treatment or prevention of parasitic infections such as pigs, cattle, horse, goat, sheep, cat, dog, poultry and fish.

In another aspect of the invention there is provided a method of preparing the composition according to the invention.

The method comprises dispersing benzimidazole carbamate particles in a mixture comprising a pharmaceutically acceptable carrier and a Tween-type surfactant and; mechanically reducing the particle size of the benzimidazole carbamate particles to an effective average particle size of less than about 450 nm.

In one embodiment the effective average particle size of the benzimidazole carbamate particles is reduced to less than about 400 nm, or about 350 nm or about 300 nm, in another embodiment to less than about 250 nm, in another embodiment to less than about 200 nm.

In one embodiment the effective average particle size of the benzimidazole carbamate particles is reduced to a particle size between about 50 nm and 450 nm, in another embodiment between about 100 nm and 400 nm, in another embodiment between about 150 and 350 nm, or between about 180 nm and 300 nm. In another embodiment the effective average particle size of the benzimidazole carbamate particles is between about 190 nm and 220 nm, in another embodiment about 200 nm.

Effective methods of providing mechanical force for particle size reduction of the benzimidazole carbamate to an effective average particle size of less than about 450 nm include ball milling, media milling, and homogenization, for example with a MICROFLUIDIZER® (Microfluidics Corp.).

In one embodiment the mechanical particle size reduction is performed by a media milling.

Ball milling is a low energy milling process that uses milling media, drug, stabilizer and liquid. The materials are placed in a milling vessel that is rotated at optimal speed such that the media cascades and reduces the drug particle size by impactation. The media used must have a high density as the energy for the particle size reduction is provided by gravity and the mass of the attrition media.

Media milling is a high energy milling process. Drug, stabilizer and liquid are placed in a reservoir and recirculated in a chamber containing media and rotating shaft/impeller. The rotating shaft agitates the media which subjects the drug to impactation and sheer forces, thereby reducing the drug particle size. A media mill is preferred due to the relatively shorter milling time required to provide the intended result, i.e., the desired reduction in particle size. In a specific embodiment a Dyno Mill Type KDL A or Dyno Mill Multi Lab available from WAB, Basel is used.

Alternative mills are Agitated Lab Ball Mill 90 AHM available from Hosokawa Alpine, Augsburg or DCP High Performance Media Mill Megavantis ACS, available from Draiswerke Inc. or DCP Superflow or Advantis perl mills from Baler.

For milling, the apparent viscosity of the premix is selected to ensure an optimal balance between efficient particle fragmentation and media erosion.

The grinding media (beads) for the particle size reduction step (wet-milling) can be selected from rigid media preferably spherical or particulate in form.

In one embodiment the grinding media have an average size less than about 1 mm In another embodiment the grinding media have an average size between 0.5 and 0.7 mm. In another embodiment the grinding media have an average size of less than 0.5 mm. In another embodiment the grinding media have an average size of 0.25 to 0.3 mm.

The selection of material for the grinding media is not believed to be critical. It is known that zirconium oxide, such as 95% or 93% ZrO stabilized with yttrium, magnesia, zirconium silicate, and glass grinding media provide particles having levels of contamination which are believed to be acceptable for the preparation of pharmaceutical compositions. However, other media, such as stainless steel, titanium and alumina, are expected to be useful. Preferred media have a density greater than about 3 g/cm$^3$.

The attrition time can vary widely and depends primarily upon the particular mechanical means and processing conditions selected. For ball mills, processing times of up to five days or longer may be required.

On the other hand, processing times of less than 1 day (residence times of one minute up to several hours) have provided the desired results using a high shear media mill, like e.g. DYNO® MILL KDL A or DYNO® MILL Multi Lab or Agitated Lab Ball Mill 90 AHM or DCP High Performance Media Mill Megavantis ACS.

The attrition time is determined according to the particle size distribution specification; it depends on many parameters such as the mill technology used, the process type (batch process or continuous process by recycling the product), the batch size, the bead size, the bead quantity, the rotation speed of the rotor and, the product flow rate.

The particles must be reduced in size at a temperature which does not significantly degrade the drug substance. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$_2$.) are typical of media milling.

Particle size reduction by homogenisation as described in U.S. Pat. No. 5,510,118 can be used alternatively as a process using a MICROFLUIDIZER® resulting in sub 450 nm particles.

For the particle size reduction the benzimidazole carbamate can be added to a liquid dispersion medium in which it is essentially insoluble to form a concentrated premix. Preferably the dispersion medium used for the particle size reduction is aqueous.

The concentration of the benzimidazole carbamate in the premix can vary from about 0.05 to about 0.6 g/ml (i.e., from about 5 to about 60% (w/v)). In some embodiments, the concentration of the benzimidazole carbamate in the premix is from about 0.15 to about 0.50 g/ml, or from about 0.2 to about 0.4 g/ml.

The premix can be used directly by subjecting it to mechanical means to reduce the average benzimidazole carbamate particle size in the dispersion to less than about 450 nm. It is preferred that the premix be used directly when a ball mill is used for attrition.

Alternatively, the benzimidazole carbamate and surfactant can be dispersed in the liquid medium using suitable agitation, e.g., a Cowles type mixer, until a homogeneous dispersion is observed in which there are no large agglomerates visible to the naked eye and diluted further. It is preferred that the premix be subjected to such a premilling dispersion step when a recirculating media mill is used for attrition.

In one embodiment a benzimidazole carbamate composition according to the current invention is prepared by using the following three manufacturing steps: preparation of a premix suspension (e.g., 0.4 g/ml FBZ), particle size reduction by wet-milling of this premix suspension to a particle size of less than 450 nm and dilution of the premix suspension with an aqueous pharmaceutical acceptable carrier to obtain the finished product (0.2 g/ml FBZ) which is the pharmaceutical composition that is directly added to the drinking water. The antifoaming agent can be added to the premix or alternatively to the aqueous carrier to prepare the finished product.

The premix compound is diluted with a pharmaceutically acceptable carrier to a concentration of the benzimidazole carbamate in the finished product of from about 5 to about 50% by weight. In some embodiments, the concentration is from about 10% to about 30% by weight, from about 15% to about 25%, or about 20% by weight.

The current invention provides a process for making the pharmaceutical composition for drinking water administration, wherein the composition comprises: benzimidazole carbamate particles having an effective average particle size of less than about 450 nm; a Tween-type surfactant; and a pharmaceutically acceptable carrier, is prepared by:
 a. dispersing the benzimidazole carbamate particles in a liquid dispersion medium comprising a Tween-type surfactant; and
 b. mechanically reducing the particle size of the benzimidazole carbamate to an effective average particle size of less than about 450 nm In one embodiment the mechanical particle size reduction is performed by a media milling.

In one embodiment the pharmaceutical composition that is obtained by the steps a) and b) above is further diluted with a pharmaceutically acceptable carrier to form the finished product that is directly added to the drinking water.

The method comprises the following steps:
 a) dispersing benzimidazole carbamate particles in a mixture comprising a pharmaceutically acceptable carrier and a Tween-type surfactant;
 b) mechanically reducing the particle size of the benzimidazole carbamate particles to an effective average particle size of less than about 450 nm to form a concentrated product mixture;
 c) adding a pharmaceutically acceptable carrier to the concentrated product form a form a diluted product; and
 d) adding the final product to drinking water.

EXAMPLES

The following examples are merely illustrative, and not limiting to the remainder of this disclosure in any way.

Example 1

Manufacturing of a Fenbendazole Composition According to the Invention

The 0.2 g/ml Fenbendazole (FBZ) drinking water suspension was prepared using the following three manufacturing steps: a) preparation of a premix suspension (0.4 g/ml FBZ), b) wet-milling of this premix suspension, and c) dilution of the premix suspension to obtain the finished product (0.2 g/ml FBZ).

Formula of the Finished Product (0.2 g/ml FBZ Suspension)

| Substance | amount |
| --- | --- |
| fenbendazole | 20.0 g |
| polysorbate 80 | 10.0 g |
| benzyl alcohol | 2.0 g |
| simethicone emulsion | 0.5 g |
| water | up to 100 ml |

A. Manufacturing of the Premix Suspension

The required amounts of simethicone emulsion and polysorbate 80 were mixed with a magnetic stirrer in a part of the water. To obtain a homogeneous mix, it was slightly heated (below 60° C.). Then the required quantity of Fenbendazole and the missing volume of water were added under a stronger stirring (Ultra-Turrax) to obtain a white and homogeneous premix suspension. To maintain the product temperature below 60° C. during the addition of fenbendazole, the beaker containing the product was kept in a cooling bath.

Formula of the Premix Suspension

| substance | amount |
| --- | --- |
| fenbendazole | 40 g |
| polysorbate 80 | 20 g |
| simethicone emulsion 30% USP | 1 g |
| purified water | up to 100 ml |

B. Wet Milling

First, the 0.6 L container of the DYNO® MILL KDL A was filled with 450 mL 0.25-0.3 mm glass beads (supplier VWR), and then 270 mL of premix suspension manufactured in step A. The premix suspension was wet-milled for 45 minutes with polyurethane discs and a rotor speed of 4200 rpm.

During the wet-milling process, the product temperature was maintained below 50° C. due to the heat transfer with the cooling double jacket.

Particle size of the Fenbendazole suspension was determined before and after milling with a Malvern Mastersizer 2000 with the Hydro 2000G measuring cell according to the following method: under stirring (stirrer speed 500 rpm, pump speed: 1000 rpm), the background of the dispersant (water) contained in the dispersing unit was measured. Then a sample of FBZ suspension was added until an obscuration of 10 to 16%. The dispersion was stirred for 2 minutes with 100% ultra-sonic before measuring the particle size distribution.

C. Dilution to Obtain the 0.2 g/ml FBZ Suspension

The volume of the wet-milled premix suspension was measured, and the required quantity of water containing 4% benzyl alcohol was added to dilute the premix suspension to obtain the 0.2 g/ml Fenbendazole (FBZ) drinking water suspension. The resulting 0.2 g/ml Fenbendazole (FBZ) drinking water suspension was used to prepare medicated water in the drinking water system Example 2

Manufacturing of a Flubendazole Composition According to the Invention

The 0.2 g/ml Flubendazole (FluBZ) drinking water suspension was prepared using the following three manufacturing steps: a) preparation of a premix suspension (0.4 g/ml FluBZ), b) wet-milling of this premix suspension, and c) dilution of the milled premix suspension to obtain the finished product (0.2 g/ml FluBZ).

Formula of the Finished Product (0.2 g/ml FluBZ Suspension)

| Substance | Amount | Supplier |
|---|---|---|
| flubendazole | 20.0 g | Transchem |
| polysorbate 80 | 10.0 g | Merck |
| benzyl alcohol | 2.0 g | Fluka |
| simethicone emulsion | 0.5 g | Dow Corning |
| purified water | up to 100 ml | — |

A. Manufacturing of the Premix Suspension

The required amounts of simethicone emulsion and polysorbate 80 were mixed with a magnetic stirrer in a part of the water. To obtain a homogeneous mix, it was slightly heated (below 60° C.). Then the required quantity of Flubendazole and the missing volume of water were added under a stronger stirring (Ultra-Turrax) to obtain a white and homogeneous premix suspension. To maintain the product temperature below 60° C. during the addition of flubendazole, the beaker containing the product was kept in a cooling bath.

Formula of the Premix Suspension

| substance | amount |
|---|---|
| flubendazole | 40 g |
| polysorbate 80 | 20 g |
| simethicone emulsion 30% USP | 1 g |
| purified water | up to 100 ml |

B. Wet-Milling

First, the 0.6 L container of the DYNO® MILL KDL A was filled with 450 mL 0.25-0.3 mm glass beads (supplier VWR), and then 270 mL of premix suspension manufactured in step A. The premix suspension was wet-milled for 45 minutes with polyurethane discs and a rotor speed of 4200 rpm.

During the wet-milling process, the product temperature was maintained below 50° C. due to the heat transfer with the cooling double jacket.

Particle size of the Flubendazole suspension was determined before and after milling with a Malvern Mastersizer 2000 with the Hydro 2000G measuring cell according to the following method: under stirring (stirrer speed 500 rpm, pump speed: 1000 rpm), the background of the dispersant (water) contained in the dispersing unit was measured. Then a sample of FBZ suspension was added until an obscuration of 10 to 16%. The dispersion was stirred for 2 minutes with 100% ultra-sonic before measuring the particle size distribution.

C. Dilution to Obtain the 0.2 g/ml FluBZ Suspension

The volume of the wet-milled premix suspension was measured, and the required quantity of water containing 4% benzyl alcohol was added to dilute the premix suspension to obtain the 0.2 g/ml Flubendazole (FBZ) drinking water suspension. The resulting 0.2 g/ml Flubendazole (FBZ) drinking water suspension was used to prepare medicated water in the drinking water system Particle Size of a Composition According to the Invention Containing FluBZ Particle Size Distribution

| | Size of 50% particles | Size of 90% particles |
|---|---|---|
| FluBZ 0.2 g/ml suspension | ≤130 nm | ≤320 nm |

Figure 10:
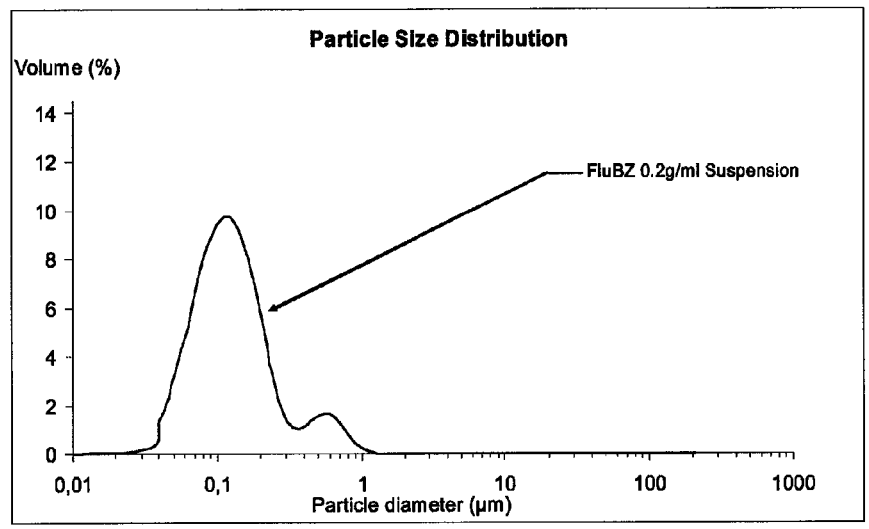
FIG. 10 represents the particle size distribution of flubendazole suspension manufactured according to Example 2

FIG. 10 graphically represents the particle size distribution of flubendazole suspension manufactured according to Example 2.

Figure 11:
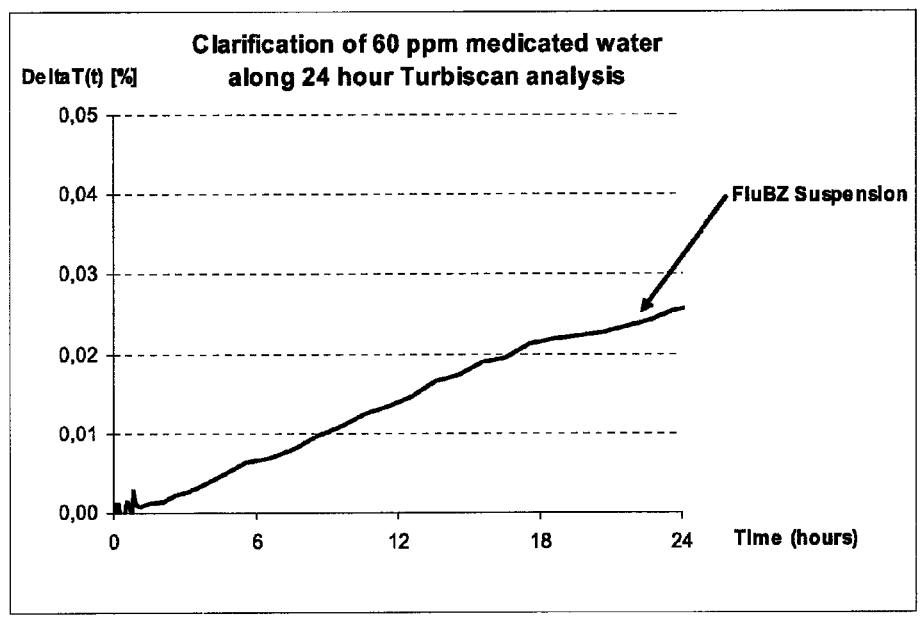
FIG. 11 represents the clarification kinetic of 60 ppm FluBZ medicated waters made with FluBZ 0.2 g/ml suspension determined by TURBISCAN® in the middle of the measuring cell for 24 hours

FIG. 11 represents the clarification kinetic of 60 ppm FluBZ medicated drinking water made with FluBZ suspension (determined by a macroscopic optical scanning device, TURBISCAN® (supplied by Formulaction, France), as described in WO 01/17504) in the middle of the measuring cell for 24 hours.

Results. No significant physical instability (clarification very below 1%, no sedimentation) was measured by TURBISCAN® for the medicated water prepared with flubendazole suspension manufactured according to Example 2 during the 24 hour.

Example 3

Alternative Wet Milling Process-Continuous Process by Recycling the Premix Suspension First, the 0.6 L container of the DYNO® MILL KDLA was filled with 450 mL 0.25-0.3 mm glass beads (supplier B. Braun Biotech International), and then about 270 mL of premix suspension manufactured in step A of Example 1 or 2.

The mill container was then connected to a pump in order to continuously feed the mill with the premix suspension; the flow rate was set at around 1.3 L/h. One wet-milling cycle was achieved when the premix suspension in its entirety (500 mL) went through the mill, was separated from the grinding media by a 0.1 mm gap and discharged in a new container. 6 milling cycles with polyurethane discs and a rotor speed of 4200 rpm were applied to the suspension premix.

During the wet-milling process, the product temperature was maintained below 50° C. due to the heat transfer with the cooling double jacket.

Particle size of the Fenbendazole suspension was determined before and after milling with a Malvern Mastersizer 2000 with the Hydro 2000G measuring cell according to the following method: under stirring (stirrer speed 500 rpm, pump speed: 1000 rpm), the background of the dispersant (water) contained in the dispersing unit was measured. Then a sample of FBZ suspension was added until an obscuration of 10 to 16%. The dispersion was stirred for 2 minutes with 100% ultra-sonic before measuring the particle size distribution. Then the wet-milled premix suspension was diluted as described in step C of Example 1 or 2.

Example 4

Alternative Wet Milling Process-Continuous Process by Recycling the Premix Suspension First, the 0.6 L container of the DYNO® MILL MULTI LAB was filled with 360 mL 0.25-0.3 mm yttrium stabilized zirconium oxide beads (supplier Mühlmeier), and then connected to a pump in order to continuously feed the mill with the premix suspension manufactured in step A of Example 1 or 2.

The flow rate was set at around 37 L/h. It was a closed loop: the premix suspension (2 L) was continuously pumped from the feeding container, brought through the mill, separated from the grinding media by a 0.1 mm gap and discharged in the feeding container. The feeding container was equipped with a stirrer to maintain the premix suspension homogeneous. 55 minutes milling with DYNO®-Accelerators and a rotor speed of 10 m/s were applied to the suspension premix. During the wet-milling process, the product temperature was maintained below 50° C. due to the heat transfer with the cooling double jacket.

Particle size of the Fenbendazole suspension was determined before and after milling with a Malvern Mastersizer 2000 with the Hydro 2000G measuring cell according to the following method: under stirring (stirrer speed 500 rpm, pump speed: 1000 rpm), the background of the dispersant (water) contained in the dispersing unit was measured. Then a sample of FBZ suspension was added until an obscuration of 10 to 16%. The dispersion was stirred for 2 minutes with 100% ultra-sonic before measuring the particle size distribution. Then the wet-milled premix suspension was diluted as described in step C of Example 1 or 2.

Example 5

Comparative Particle Size of a Composition According to the Invention and a Composition Manufactured According to WO 95/13065

A composition according to WO 95/13065 was prepared as described in Example 1 Step A. The particle size was determined without (composition according to WO 95/13065 and after wet-milling (composition according to the invention prepared according to Example 1 Steps A-B)) with a Malvern Master sizer GMAL 01 with the Hydro 2000G measuring cell according to Frauenhofer method. The wet-milling resulted in a particle size reduction of the fenbendazole particles to an effective particle size of less than 200 nm.
Particle Size Distribution Without and After Wet Milling

|  | D(0.50) | D(0.90) |
| --- | --- | --- |
| FBZ crude suspension | ≤2440 nm | ≤32640 nm |
| FBZ 0.2 g/ml suspension | ≤120 nm | ≤200 nm |

FIG. 1 graphically represents the particle size distribution without and after wet-milling.

Figure 2:
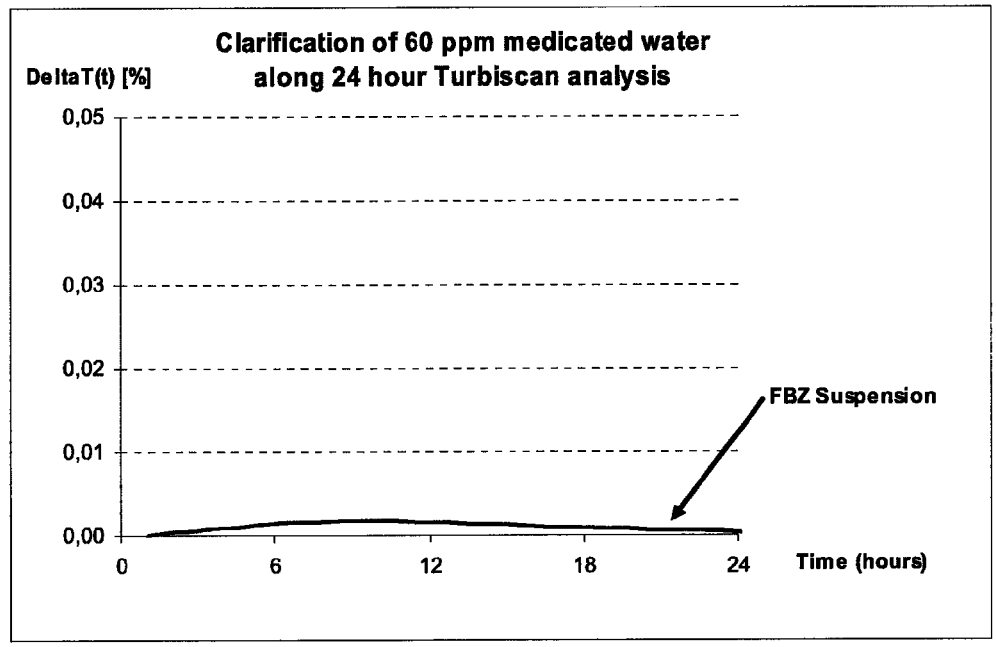
FIG. 2 represents the clarification kinetic of 60 ppm FBZ medicated drinking water made with FBZ suspension after wet-milling, determined by TURBISCAN® in the middle of the measuring cell for 24 hours.

FIG. 2 represents the clarification kinetic of 60 ppm FBZ medicated drinking water made with FBZ suspension (determined by a macroscopic optical scanning device, TURBISCAN® (supplied by Formulaction, France), as described in WO 01/17504) in the middle of the measuring cell for 24 hours.

The TURBISCAN® equipment detects any change (e.g., clarification, sedimentation, etc.) in dispersed systems on the basis of multiple light scattering. It is a vertical scan macroscopic analyser consisting of a reading head moving along a flat-bottomed cylindrical cell, while scanning the entire sample height. The reading head itself consists of a pulsed near infrared light source and two synchronous detectors: the transmission detector picks up the light transmitted through the product and the backscattering detector receives the light backscattered by the product. The reading head acquires transmission and backscattering data every 40 µm on a maximum height of 80 mm. The profile obtained characterises the product homogeneity, particles concentration and mean diameter. Results are represented by the percentage of backscattered or transmitted light as a function of the sample height (in mm). The acquisition along the product is then repeated with a programmable frequency to obtain a superimposition of product fingerprints characterising the stability or instability of the product, whether they are identical or not.

Results. No sign of physical instability (no clarification, no sedimentation) was measured by TURBISCAN® for the medicated water prepared with fenbendazole suspension manufactured according to Example 1 during the 24 hour.

Example 6

Comparative Physical Stability of a Composition According to the Invention and a Composition Manufactured According to WO 95/13065

A composition according to the invention, called "FBZ suspension more wet-milled" was manufactured as described in Example 1. A fenbendazole suspension was manufactured as described in WO 95/13065 (called "FBZ crude suspension"). A composition, called "FBZ suspension slightly wet-milled" was prepared according the same manufacturing steps as described in Example 1, but with softer wet-milling conditions: 1 L of premix suspension was milled with 490 ml of 0.5 mm glass beads for only 3 milling cycles with polyurethane discs and a rotor speed of 3200 rpm. These wet-milling conditions permitted to obtain an intermediate particle size distribution compared to the "FBZ suspension more wet-milled" and the FBZ crude suspension.
Particle Size Distribution of FBZ Crude Suspension (not Wet Milled) and FBZ Suspensions (Slightly and More Wet Milled)

|  | D(0.50) | D(0.90) |
| --- | --- | --- |
| FBZ crude suspension (according to WO 95/13065) FBZ 0.2 g/ml suspension | ≤2430 nm | ≤24710 nm |
| slightly wet milled | ≤350 nm | ≤1030 nm |
| more wet milled | ≤120 nm | ≤200 nm |

Figure 3:
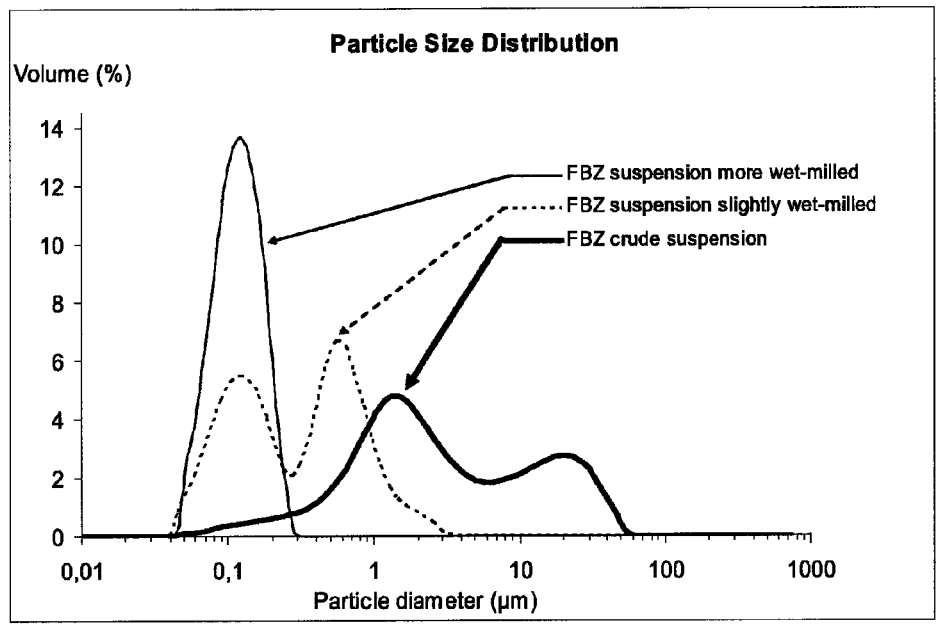
FIG. 3 represents the particle size distribution of FBZ crude suspension (not wet-milled) and FBZ suspensions (slightly and more wet-milled)

FIG. 3 graphically represents these particle size distributions.

The preparations were diluted with water to obtain a concentration of 60 ppm fenbendazole like, for example, medicated water for poultry treatment. The physical stability of the resulting medicated water was studied with the help of the macroscopic optical scanning device TURBISCAN® as described in Example 5.

Figure 4:
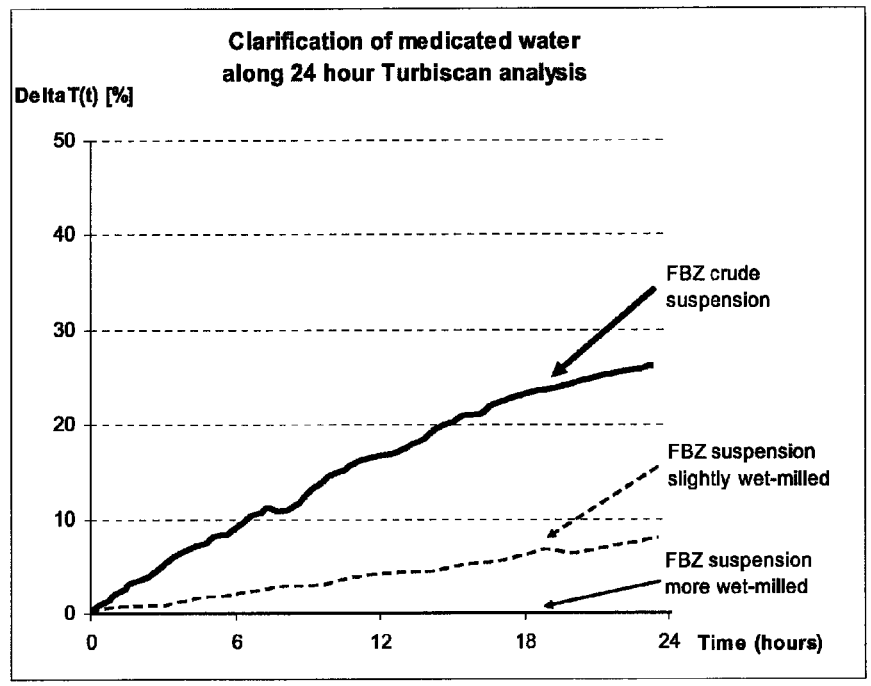
FIG. 4 represents clarification kinetic of 60 ppm FBZ medicated drinking water made with FBZ crude suspension (not wet-milled) and FBZ suspensions (slightly and more wet-milled), determined by TURBISCAN® in the middle of the measuring cell for 24 hours

The results of the TURBISCAN® evaluation are illustrated in FIG. 4, which show the kinetic of clarification detected in the middle of the measuring cell for 24 hours for each of the three preparations.

Results. No sign of physical instability was measured by TURBISCAN® for the medicated water prepared with fenbendazole suspension, manufactured according to Example 1 during the 24 hour analysis, whereas a significant clarification occurred with the medicated water prepared with fenbendazole crude suspension manufactured according to WO 95/13065. This clarification corresponds to the formation of a sediment layer detectable about 6.5 hours after the start of the study. The slightly wet-milled suspension displayed an intermediate stability profile. Its clarification level matched with the detection of a sediment layer only after 14 hours at rest.

Example 7

Comparative Physical Stability of a Composition According to the Invention and a Commercial Suspo-Emulsion Product (SOLUBENOL®, Janssen-Cilag, Beerse Belgium)

Figure 5:
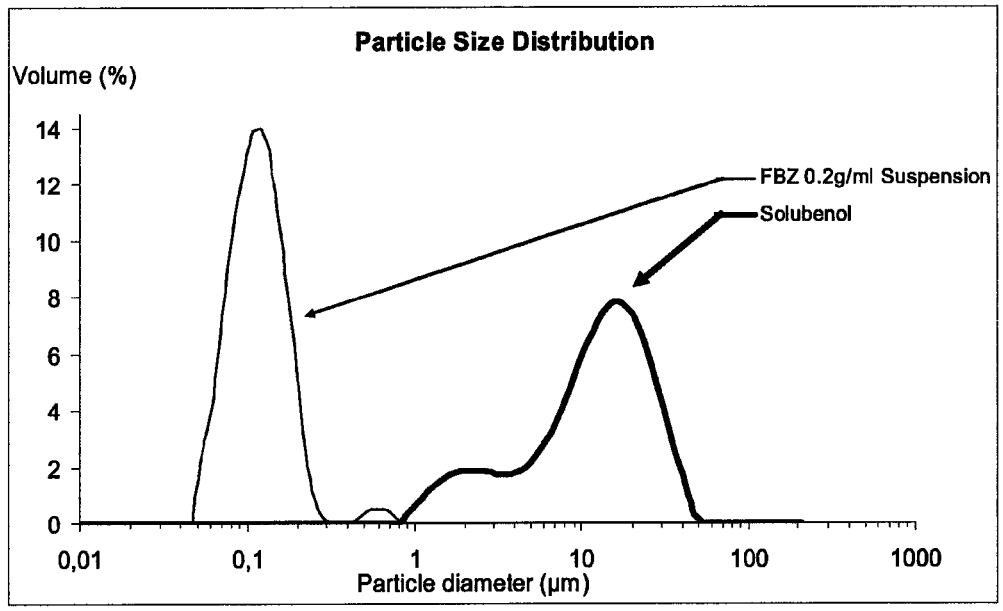
FIG. 5 represents particle size distribution of SOLUBENOL and FBZ suspension

The commercial suspo-emulsion product SOLUBENOL® was diluted with water to obtain a concentration of 85.6 ppm flubendazole like, for example, medicated water for poultry treatment. Its particle size distribution is summarized in the Table below, and graphically represented in FIG. 5 with the composition according to the invention (FBZ suspension) described in Example 1 as reference.

Particle Size Distribution of FBZ 0.2 g/ml Suspension Compared to SOLUBENOL®

|  | D(0.50) Size of 50% particles | D(0.90) Size of 90% particles |
|---|---|---|
| SOLUBENOL ® | ≤13700 nm | ≤29800 nm |
| FBZ 0.2 g/ml suspension | ≤120 nm | ≤200 nm |

Figure 6:
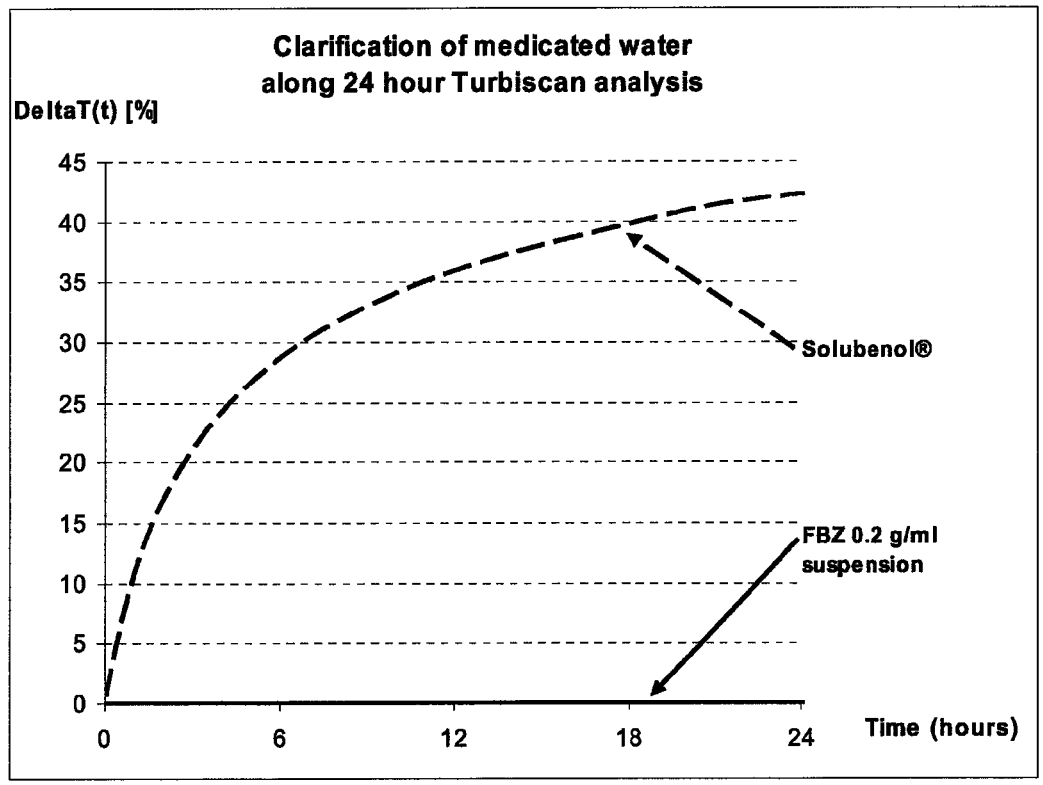
FIG. 6 represents clarification kinetic of 85.6 ppm Flubendazole medicated water made with SOLUBENOL® and 60 ppm FBZ medicated water made with FBZ suspension, determined by TURBISCAN® in the middle of the measuring cell for 24 hours

The physical stability of medicated water prepared with SOLUBENOL® was studied with the help of the TURBISCAN® according to the same analysis instructions as in Example 2. The results of the TURBISCAN® evaluation are illustrated in FIG. 6, which show the kinetic of clarification detected in the middle of the measuring cell for 24 hours for the medicated water prepared with the SOLUBENOL® preparation. Results. A significant clarification occurred with SOLUBENOL® medicated water, whereas no sign of physical instability was measured by TURBISCAN® for the medicated water prepared with a fenbendazole suspension manufactured according to Example 1 during the 24 hour analysis.

Example 8

Fenbendazole Suspension Manufactured with Various Surfactants

FBZ suspensions were manufactured as described in Example 1 with the following ingredients.

| Substance | Function | Company |
|---|---|---|
| Fenbendazole | Active ingredient | Intervet |
| a) Polysorbate 20 | Suspending agent | Merck |
| b) Polysorbate 40 | Suspending agent | Merck |
| c) Polysorbate 60 | Suspending agent | Merck |
| d) Polysorbate 80 | Suspending agent | VWR |
| e) Poloxamer 188 | Suspending agent | Uniqema |
| Simethicone emulsion 30% USP | Defoaming agent | Dow Corning |
| Benzyl alcohol | Preservative | Fluka |
| Purified water | Up to 100 ml | |

Physical Stability Evaluation of Medicated Water

The FBZ suspensions with the suspending agents were diluted to 60 ppm with water just before analysis and the physical stability (transmitted and backscattered light) of the different medicated waters over 24 hours at room temperature were measured with Turbiscan. The premix suspension containing Poloxamer 188 was manufactured with the following deviations in comparison with the process described in Example 1. Poloxamer 188 was melt before being mixed with simethicone emulsion and then by the addition of fenbendazole, the mixture became so viscous while stirring that it was not feasible to pass it through the mill.

Particle Size Distribution

Particle size distribution of the various suspensions was measured before and after wet-milling and reported in the table below.

| FBZ suspension | Particle size distribution (μm) | | | | | |
|---|---|---|---|---|---|---|
| | Before wet-milling | | | After wet-milling | | |
| | D(0.50) | D(0.90) | D(0.95) | D(0.50) | D(0.90) | D(0.95) |
| with Polysorbate 20 | 1.89 | 17.74 | 23.74 | 0.12 | 0.25 | 0.37 |
| with Polysorbate 40 | 2.18 | 28.39 | 49.69 | 0.13 | 0.32 | 0.81 |
| with Polysorbate 60 | 2.06 | 26.85 | 41.07 | 0.13 | 0.33 | 0.62 |
| with Polysorbate 80 | 2.44 | 32.64 | 50.46 | 0.12 | 0.20 | 0.23 |
| with Poloxamer 188 | 2.23 | 29.03 | 41.84 | — | — | — |

All the polysorbate compositions presented a fine and narrow particle size distribution after wet-milling.

Physical Stability Evaluation of Medicated Water

Figure 7:
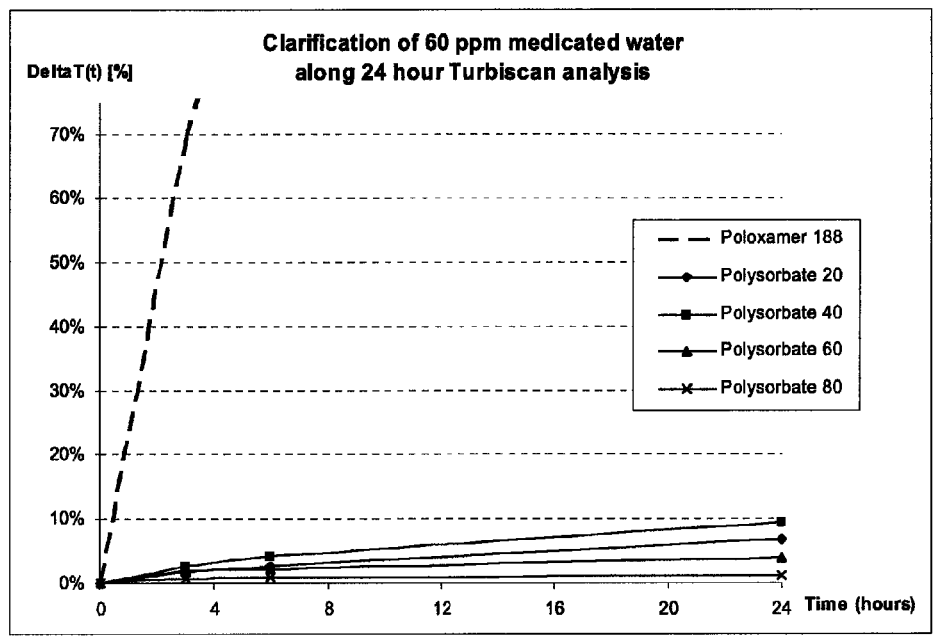
FIG. 7 represents the physical stability of 60 ppm FBZ medicated water medicated water issued from the dilution of FBZ suspension containing various surfactants determined by TURBISCAN® in the middle of the measuring cell for 24 hours

The FBZ suspensions with the suspending agents were diluted to 60 ppm with water just before analysis and the physical stability (transmitted and backscattered light) of the different medicated waters over 24 hours at room temperature were measured with TURBISCAN®according to the same analysis instructions as in Example 3. The results of the TURBISCAN® evaluation are illustrated in FIG. 7, which show the kinetic of clarification detected in the middle of the measuring cell for 24 hours for the medicated waters prepared with the FBZ 0.2 g/ml Suspensions containing the various suspending agents.

Results. The medicated water issued from the dilution of the FBZ suspension containing Poloxamer 188 is physically unstable. It was confirmed by the detection of a sediment layer which grows at 0.77 μm/min whereas no sediment layer could be detected for the other medicated waters containing various Polysorbates.

Medicated water with tested polysorbates display an acceptable transmission variation below 10% for 24 hours.

Example 9

Fenbendazole Suspension Manufactured with Various Concentrations of Polysorbate 80

FBZ suspensions were manufactured as described in Example 1 with the following ingredients.

| | | |
|---|---|---|
| Fenbendazole | Active ingredient | 20.0 g |
| Polysorbate 80 | Suspending agent | 5, 10 or 15 g |
| Simethicone emulsion 30% USP | Defoaming agent | 0.5 g |
| Benzyl alcohol | Preservative | 2.0 g |
| Purified water | | Up to 100 ml |

Particle Size Distribution

Particle size distribution of the various FBZ suspensions was measured before and after wet-milling and reported in the table below.

| | Particle size distribution (µm) | | | | | |
|---|---|---|---|---|---|---|
| | Before wet-milling | | | After wet-milling | | |
| FBZ Suspension | D(0.50) | D(0.90) | D(0.95) | D(0.50) | D(0.90) | D(0.95) |
| with 5% Polysorbate 80 | 2.45 | 32.08 | 55.87 | 0.13 | 0.20 | 0.22 |
| with 10% Polysorbate 80 | 2.44 | 32.64 | 50.46 | 0.12 | 0.20 | 0.23 |
| with 15% Polysorbate 80 | 2.16 | 30.64 | 51.10 | 0.11 | 0.19 | 0.22 |

All the FBZ suspensions presented a fine and narrow particle size distribution after wet-milling.

Physical Stability Evaluation of Medicated Waters

The FBZ suspensions with the suspending agents were diluted to 60 ppm with water just before analysis and the physical stability (transmitted and backscattered light) of the different medicated waters over 24 hours at room temperature were measured with Turbiscan. The physical stability of medicated water was studied with the help of the TURBISCAN® according to the same analysis instructions as in Example 5.

Figure 8:
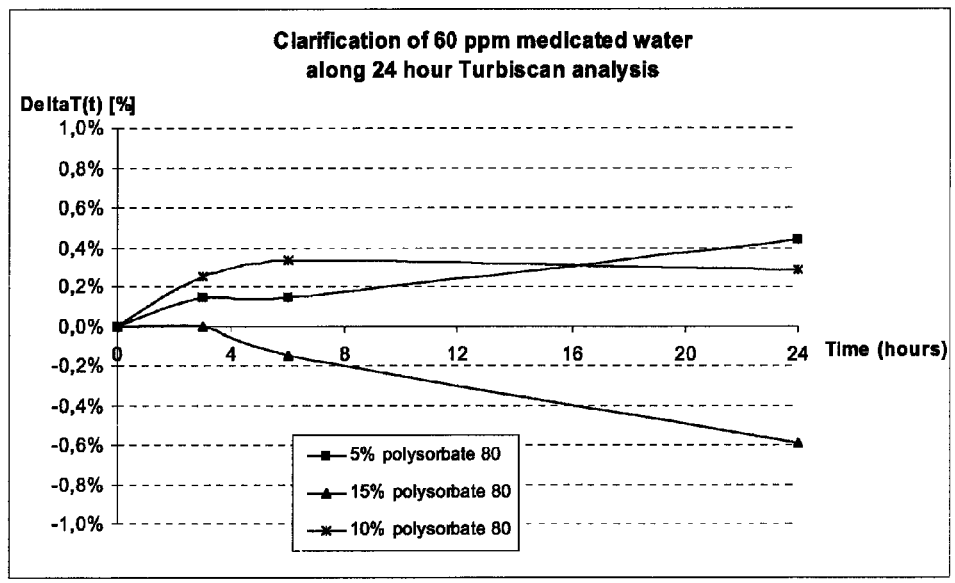
FIG. 8 represents the physical stability of 60 ppm FBZ medicated water medicated water issued from the dilution of FBZ suspension containing various concentrations of Polysorbate 80 determined by TURBISCAN® in the middle of the measuring cell for 24 hours

The results of the TURBISCAN® evaluation are illustrated in FIG. 8, which shows the kinetic of clarification detected in the middle of the measuring cell for 24 hours for the medicated waters prepared with the FBZ 0.2 g/ml Suspensions containing the various concentrations of polysorbate 80.

Results: No sediment layer could be detected for the medicated waters containing the different concentrations of Polysorbate 80. This good physical stability is confirmed by the transmission variation graph: the maximum variation corresponds to 1% after 24 hour which is acceptable.

Example 10

Wet-Milling of Fenbendazole 20% and 40% Suspension

A composition according to the invention, called "FBZ 0.2 g/ml suspension" was manufactured as described in Example 3.

A fenbendazole suspension was manufactured as described in WO 95/13065 (called "FBZ crude suspension") and wet-milled as follows.

First, the 0.6 L container of the DYNO® MILL MULTI LAB was filled with 360 mL 0.3 mm yttrium stabilized zirconium oxide beads (supplier Mühlmeier), and then connected to a pump in order to continuously feed the mill with FBZ crude suspension. The flow rate was set at around 112 L/h. It was a closed loop: the premix suspension (2 L) was continuously pumped from the feeding container, brought through the mill, separated from the grinding media by a 0.1 mm gap and discharged in the feeding container. The feeding container was equipped with a stirrer to maintain the premix suspension homogeneous. 55 minutes milling with DYNO®-Accelerators and a rotor speed of 10 m/s were applied to the suspension premix.

During the wet-milling process, the product temperature was maintained below 50° C. due to the heat transfer with the cooling double jacket.

The particle size distribution of the Fenbendazole suspensions was measured as described in Example 3.

Particle Size Distribution of FBZ 0.2 g/ml Suspension Compared to the Wet-Milled FBZ Crude Suspension

| | D(0.50) | D(0.90) |
|---|---|---|
| wet-milled FBZ crude suspension | ≤130 nm | ≤300 nm |
| FBZ 0.2 g/ml suspension | ≤130 nm | ≤290 nm |

Results. Milling the final product "FBZ crude suspension" containing 20% w/v FBZ or milling the premix suspension containing 40% FBZ to be diluted to obtain the final product "FBZ 0.2 g/ml suspension" resulted in equivalent particle size distribution.

Example 11

Pipe Trial with Fenbendazole Suspension

A composition according to the invention, called "FBZ 0.2 g/ml suspension" was manufactured as described in Example 2 (the milling step was performed with 420 mL 0.3 mm yttrium stabilized zirconium oxide beads from Mühlheimer, two cycles with a flow rate of 1 L/h were performed).

Particle Size Distribution of FBZ 0.2 g/ml Suspension Compared to the FBZ Crude Suspension

| | D(0.50) | D(0.90) |
|---|---|---|
| FBZ crude suspension | ≤1910 nm | ≤13180 nm |
| FBZ 0.2 g/ml suspension | ≤130 nm | ≤270 nm |

A fenbendazole suspension was manufactured as described in WO 95/13065 (called "FBZ crude suspension"). The particle size distribution of the Fenbendazole suspensions was measured as described in Example 3.

The stability and the homogeneity of medicated water made with both compositions were tested for a 3-hour period by simulating medicated water distribution in field conditions. These studies were conducted with drinking water from the local water supply.

Medicated water was prepared with the required amount of the composition and drinking water in the medication tank in order to obtain a concentration of 60 ppm fenbendazole like, for example, medicated water for poultry treatment. The tank was connected to a 25-m transparent pipe via the bottom outlet of the tank. The flow rate was set at approximately 3.5

L/h. Medicated water was periodically sampled in the medication tank (at the surface) and at the end of the 25-m pipe during the distribution period.

Figure 9:
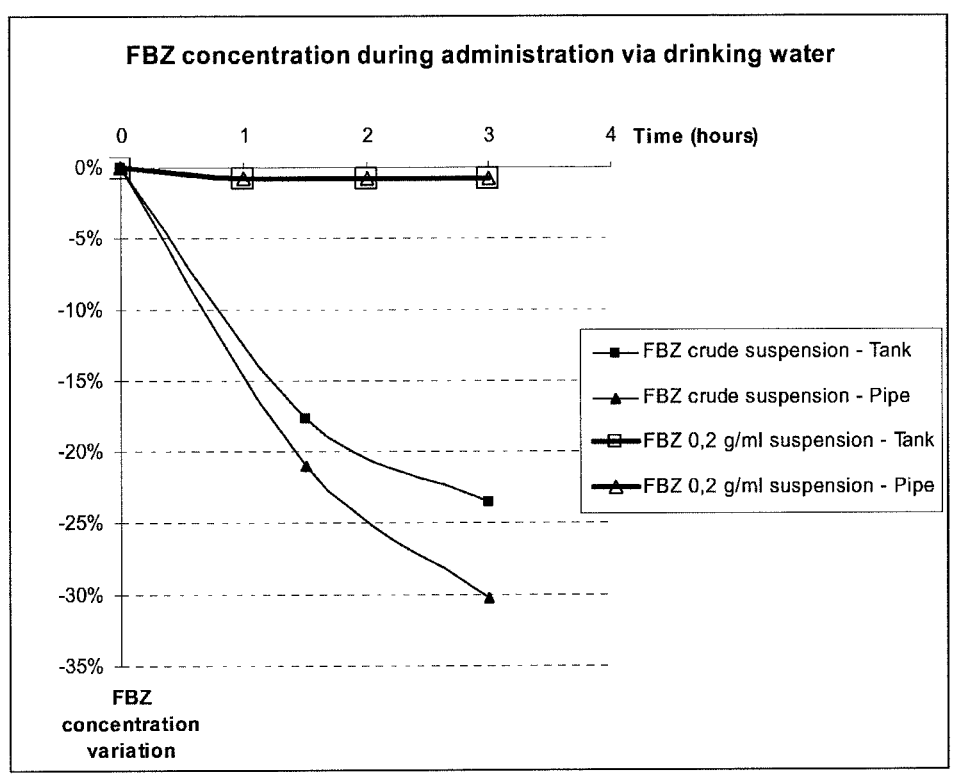
FIG. 9 represents the FBZ concentration in medicated waters prepared with FBZ crude suspension and FBZ 0.2 g/ml suspension along 3 hour distribution; samples were taken from medication tank and at the end of the 25 m pipe

The samples were analyzed in terms of fenbendazole content. Medicated water was not stirred during the distribution period. Furthermore, the medication tank and the pipe were checked visually for any sediment formed. The results are illustrated in FIG. 9, which shows the FBZ concentration variation of both medicated waters sampled from the medication tank and the pipe end.

Results. In both studies, no sediments were detected in the medication tank and the pipe; however in the medication tank containing FBZ crude suspension medicated water, the medicated water looked more concentrated at the bottom of the tank at the end of the trial. This instability was confirmed by the analytical results which showed a dramatic decrease of FBZ concentration along the distribution period for the medicated water prepared with the FBZ crude suspension in contrast to the homogeneous and stable medicated water prepared with FBZ 0.2 g/ml suspension.

Example 12

Field Trial Pig and Poultry

A composition according to the invention, called "FBZ 0.2 g/ml suspension" was manufactured as described in Example 1. Two field studies were conducted to evaluate the homogeneity and stability of the FBZ 0.2 g/ml suspension in medicated water when used under field conditions.

One study was conducted in growing pigs with a medication tank, a closed loop water system (made of PVC and stainless steel pipes) of approximately 60 m long and the other one in growing turkeys with an electronic dosing pump (KONTI-DOS from Buerkert) and a dead end water supply system (made of galvanized iron and plastic pipes) of about 220 m long.

The general study procedures were the same for each study: medicated water was prepared using the drinking water available on the farms with pH values ranging between 7.2-8.2 and total hardness ranging between 7.3 and 13.7° dH. Concentrations of FBZ in water were prepared in parts per million (ppm) based on a single dose of 5 mg FBZ/kg bodyweight, the animals' bodyweights and the estimated water consumption over three (medication tank) and eight (dosing pump) hours.

Samples of medicated water were taken every 30 to 60 minutes during administration from the bottom and the top of the tank and at predefined nipples and drinkers along the water supply system. The content of the tank was not stirred throughout the whole administration period.

Tank and nipples or drinkers were inspected for any kinds of sediments formed by the active or any of the excipients.

Additional water samples were drawn approximately 24 hours after cessation of administration to assess for potential residues of FBZ content. All water samples were subsequently analyzed for FBZ content using a validated HPLC method.

Results. All analytical results (actual FBZ concentrations) were in line with the nominal (calculated) concentrations. Consistent FBZ concentrations were achieved in the tanks and along the water pipes over two or eight hours of administration. There was no difference in FBZ concentrations in samples taken from the bottom and the top of the tanks.

In the tanks, no sedimentation or floating of particles was observed. No sedimentation or blocking of nipples occurred. The water samples taken 24 hours after cessation of administration did not show any measurable residues of FBZ (below limit of detection of approximately 0.4 ppm), indicating that new FBZ suspension does not form any residues in the drinking water systems. The results from these field studies are summarized in the following table.

Mean FBZ Concentrations Reported from the Field Studies

| | | Mean FBZ concentrations [ppm] over time | | | | | | |
| --- | --- | --- | --- | --- | --- | --- | --- | --- |
| | | medication/predilution tank | | nipples/drinkers | | | | |
| Study | conc. | A1 | A2 | B | C | D | E | F | G |
| Pigs | nominal | | | | 192 | | | | |
| | actual | 193.3 | 188.3 | 180.6 | 181.7 | 193.3 | 186.7 | 176.0 | 190.3 |
| Turkey | nominal | 2395 | | | | 81 | | | |
| | actual | 2443.4 | 2413.1 | 82.7 | 84.6 | 78.4 | 83.3 | 72.2 | 76.8 |

The conclusion from these field studies is that the FBZ 0.2 g/ml suspension is homogeneously distributed in medicated water in representative water supply systems of the selected pig and poultry farms and that an accurate dosing is ensured during administration as consistent FBZ concentrations were produced over the defined administration period.

The words "comprise," "comprises," and "comprising" in this patent (including the claims) are to be interpreted inclusively rather than exclusively. This interpretation is intended to be the same as the interpretation that these words are given under United States patent law. All references cited in this patent are incorporated by reference into this patent.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A method for protecting an animal from helmith parasite infection by administering medicated drinking water to such animal via a drinking water system, such medicated drinking water comprises a stable aqueous suspension of benzimidazole carbamate particles wherein at least 90% of the benzimidazole carbamate particles have an weight average particle size of less than about 450 nm.

2. The method of claim 1, wherein at least 90% of the benzimidazole carbamate particles have a weight average particle size of less than about 300 nm.

3. The method of claim 1, wherein the benzimidazole carbamate comprises fenbendazole.

4. The method of claim 1, wherein the drinking water system comprises a medication tank.

5. The method of claim 1, wherein the drinking water system comprises a dosing pump system.

6. The method of claim 1 comprising the steps of:

a. adding a pharmaceutical composition comprising an aqueous suspension comprising benzimidazole carbamate particles and a TWEEN type surfactant wherein at least 90% of the benzimidazole carbamate particles have an weight average particle size of less than about 450 nm to a medication tank or dosing pump system of a drinking water system;

b. forming medicated drinking water in such drinking water system providing from about 1 mg to about 5 mg of benzimidazole carbamate per kilogram bodyweight of the animals being treated per day in the volume of drinking water normally consumed by the animals in a 2 to 24 hour treatment period and;

c. allowing the animals access to the medicated drinking water for from about 2 hours to 24 hours on one to six consecutive days.

7. A medicated drinking water for animals comprising from about 10 to about 150 ppm of benzimidazole carbamate particles in an aqueous suspension, wherein at least 90% of the benzimidazole carbamate particles have a weight-average particle size of less than about 450 nm, and wherein a sediment layer comprising the benzimidazole carbamate particles does not form in the medicated drinking water about 6.5 hours after dilution of the benzimidazole carbamate particles into the drinking water.

8. The medicated drinking water of claim 7, wherein at least 90% of the benzimidazole carbamate particles have a weight average particle size of less than about 300 nm.

9. The medicated drinking water of claim 7, wherein the benzimidazole carbamate comprises fenbendazole.

10. The medicated drinking water of claim 7, wherein the benzimidazole carbamate particles do not form a sediment layer in the drinking water until at least 14 hours after dilution.

11. The medicated drinking water of claim 7, wherein the benzimidazole carbamate particles do not form a sediment layer in the drinking water for at least 24 hours after dilution.

12. A method for preparing medicated drinking water according to claim 7, wherein the method comprises:

a. dispersing benzimidazole carbamate particles in a mixture comprising a pharmaceutically acceptable carrier and a TWEEN-type surfactant; and b. mechanically reducing the particle size of the benzimidazole carbamate particles to an effective average particle size of less than 450 nm, thereby forming a pharmaceutical composition, c. adding a pharmaceutically acceptable carrier to the pharmaceutical composition to form a diluted product; and d. adding the diluted product to drinking water.

13. The method according to claim 12, wherein mechanical particle size reduction is performed by media milling.

14. The method according to claim 12, wherein the pharmaceutically acceptable carrier is water.

15. The method according to claim 12, wherein the effective average particle size is less than about 300 nm.

16. The method according to claim 12, wherein the TWEEN-type surfactant comprises Polysorbate 80.

17. The method according to claim 12, wherein the benzimidazole carbamate comprises fenbendazole.

18. The method according to claim 12, wherein the benzimidazole carbamate comprises flubendazole.

* * * * *